(12) United States Patent
Johnson

(10) Patent No.: US 9,429,486 B2
(45) Date of Patent: Aug. 30, 2016

(54) STRAIN SENSOR USING SAW TECHNOLOGY

(71) Applicant: Mnemonics, Inc., Melbourne, FL (US)

(72) Inventor: Fred Johnson, Pleasanton, CA (US)

(73) Assignee: Mnemonics, Inc., Melbourne, FL (US)

( * ) Notice: Subject to any disclaimer, the term of this patent is extended or adjusted under 35 U.S.C. 154(b) by 82 days.

(21) Appl. No.: 14/275,128

(22) Filed: May 12, 2014

(65) Prior Publication Data

US 2015/0013468 A1    Jan. 15, 2015

Related U.S. Application Data

(60) Provisional application No. 61/822,360, filed on May 11, 2013.

(51) Int. Cl.
*G01L 1/10* (2006.01)
*G01N 3/08* (2006.01)

(52) U.S. Cl.
CPC .. *G01L 1/10* (2013.01); *G01N 3/08* (2013.01)

(58) Field of Classification Search
CPC ........ G01N 3/08; G01N 29/022; G01L 1/10; G01L 1/165; G01K 11/265; H01L 41/1132
USPC ......... 73/778, 715, 702, 703, 654, 599, 178, 73/706, 763, 514, 775, 774, 862.629, 73/862.636, 862.637
See application file for complete search history.

(56) References Cited

U.S. PATENT DOCUMENTS

| | | |
|---|---|---|
| 4,096,740 A | 6/1978 | Sallee |
| 7,165,455 B2 | 1/2007 | Magee |
| 8,186,232 B2 | 5/2012 | McDearmon |
| 8,258,674 B2 | 9/2012 | Olariu |
| 8,421,314 B2 | 4/2013 | Kobayashi et al. |
| 8,639,934 B2 | 1/2014 | Kruglick |
| 2013/0228616 A1 | 9/2013 | Bhosle |

*Primary Examiner* — Harshad R Patel
*Assistant Examiner* — Brandi N Hopkins
(74) *Attorney, Agent, or Firm* — John L. DeAngelis; Beusse Wolter Sanks & Maire PLLC

(57) ABSTRACT

A strain sensor for determining a strain experienced by a body under test in response to forces exerted on the body-under-test. The strain sensor comprises an interface member mounted on a surface of the body-under-test and a SAW sensor mounted on a surface of the interface member. The strain in the body-under-test is translated to strain in the SAW sensor and determined by the SAW sensor. The strain in the SAW sensor is responsive to the strain in the body-under-test.

19 Claims, 4 Drawing Sheets

STRAIN SENSOR USING SAW TECHNOLOGY

CROSS REFERENCE TO RELATED APPLICATION

This patent application claims benefit of the May 11, 2013 filing date of provisional patent application No. 61/822,360, which is incorporated by reference herein.

FIELD OF THE INVENTION

The present invention relates to surface acoustic wave devices (SAW devices) and specifically to SAW devices for use in measuring material deformation (strain) or stress forces imposed on a body-under-test or a material-under-test.

BACKGROUND OF THE INVENTION

Stress is related to a force imposed on a material or body and strain is the deformation of the material or body responsive to that stress force. The force that produces the stress can be compressive or tensile. Stress is defined as $$\sigma = F/A$$

where $\sigma$ is the stress, F is the force imposed on the material or body and A is the area over which that force is exerted.

The relationship between the stress and the resulting strain as manifested by a specific material is referred to as the stress-strain curve for that material. The curve is unique for each material and relates the amount of deformation (strain) at various values of tensile or compressive loading (stress). These curves reveal many of the properties of a material, including data to establish the materials modulus of elasticity (Young's modulus).

Strain is a dimensionless quantity that is a measure of body deformation representing the displacement of particles in the body relative to a reference length or another reference dimension. Strain measures are usually expressed as a percent or a decimal fraction of the reference dimension when no stress forces are present. For example, $\Delta L/L$ is a ratio indicating strain, where $\Delta L$ is a measure of a change in a body dimension (deformation due to compression for example) and L is a measure of the body dimension when no stress forces are present.

A passive SAW (surface acoustic wave) device comprises a transducer that generates an acoustic wave in response to an input signal, for example an interrogation signal. The waves propagate on the surface of a material (referred to as a substrate and which may comprise lithium niobate, for example) to a reflector array. The acoustic waves reflect from the reflector array back to the transducer where they are received and processed. The characteristics of the reflected wave are responsive to physical parameters of the reflector array. For example, spacing of the reflectors or elements of the reflector array are affected by a temperature of the material, which may in turn be affected by an ambient temperature of the region surrounding the SAW device.

Characteristics of the reflected waves (e.g., time delay, propagation losses, phase delay) indicate certain characteristics of the substrate or a material to which the substrate is affixed. These characteristics may include temperature, forces exerted, and resulting stresses. As the spacing of the reflector array elements changes the frequency of the reflected wave, either primary or secondary, may also be affected. Displacement can be measured in this way.

FIG. 1 depicts a prior art SAW device 10 (also referred to as a SAW sensor). An interrogating signal comprises a radio frequency (RF) signal pulse 12 transmitted by an RF transceiver 14. The interrogating signal is received by an antenna 18 connected to an interdigital transducer (IDT) 20 disposed on a piezoelectric substrate 24. The IDT 20 launches an incident surface acoustic wave (SAW) 28 onto the piezoelectric substrate 24 in response to the received interrogating signal. The transmitted wave travels along the surface of the piezoelectric substrate 24 as illustrated in FIG. 1.

The SAW 28 propagates along the substrate 24 and is received at a reflector array 30 also disposed on the piezoelectric substrate 24. The reflector array 30 comprises a pattern of metal electrodes (also referred to as elements) that impart an impulse response to the incident SAW 28. The impulse response of the reflector array 30 is imparted to the incident SAW 28 as it launches a reflected SAW 34 back to the IDT 20.

The IDT 20 receives and converts the reflected SAW 34 to an electrical signal that is then radiated from the antenna 18 back to the RF transceiver 14 for extraction of the desired information in the reflected signal.

A SAW device can sense piezoelectric crystal strain as the strain modifies the reflector array 30 and thus the reflected signal. For example, either the frequency shift of the reflected signal or the time delay of the reflected signal can be measured as an indication of the strain.

This technique provides a wireless strain sensor that can be mounted onto translating or rotating components where wire or other physical connections are not practical.

One fundamental difficulty associated with using a conventional SAW device to measure strain is the very small strain-to-failure property for LNB (lithium niobate) and similar piezoelectric substrates on which SAW devices are fabricated. The elastic strain limits of the piezoelectric crystals are typically about 0.1%. Many metals can withstand (that is, without plastic deformation) strains of up to about 0.2% in the elastic range. Other metals and certain materials, especially composites, can withstand strains in excess of about 0.5% in the elastic range. Elastomeric materials can withstand stress forces inducing strains exceeding 200%.

BRIEF DESCRIPTION OF THE DRAWINGS

The invention is explained in the following description in view of the drawings that show.

DETAILED DESCRIPTION OF THE INVENTION

In its various embodiments the present invention employs techniques and associated components to translate larger strains imposed on a body-under-test into strains acceptable and tolerable to a conventional SAW device.

Figure 1:
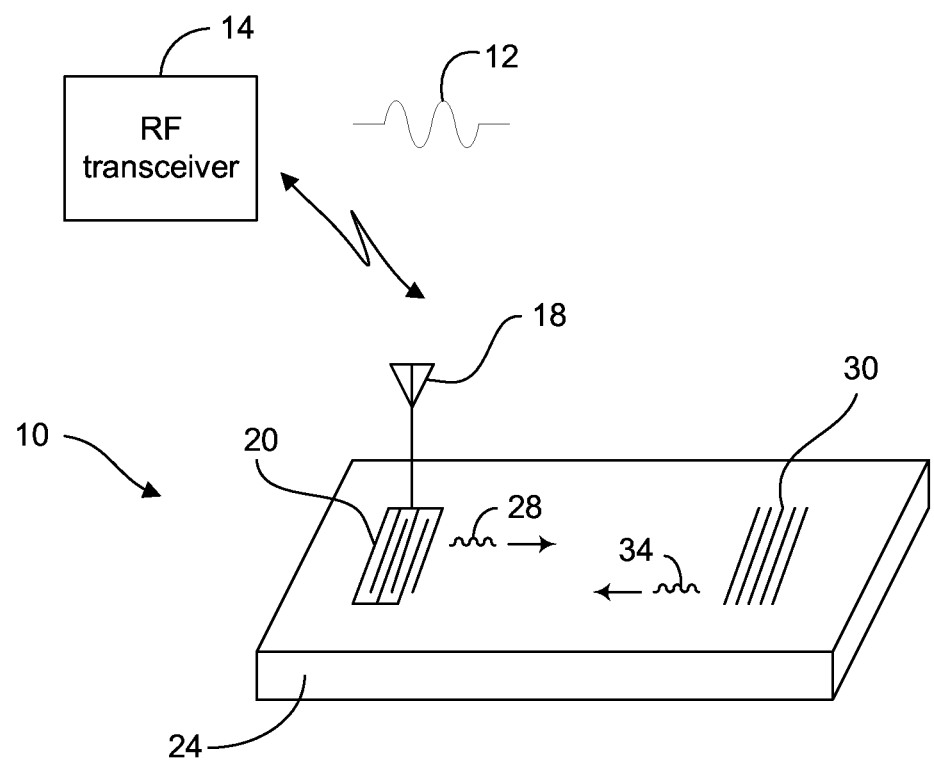
FIG. 1 illustrates a prior art surface acoustic wave device.
Figure 2:
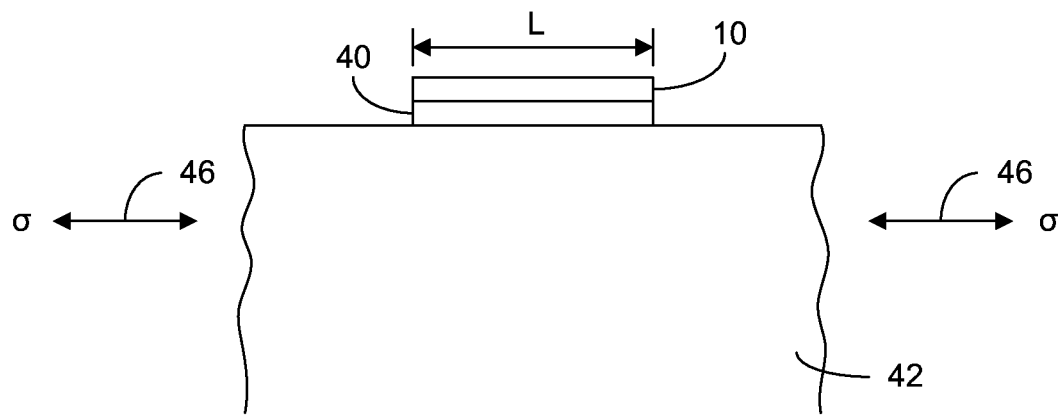
FIGS. 2 and 3 illustrate components for measuring a stress imposed on or a resulting strain deformation of a body-under-test.

FIG. 2 illustrates a conventional SAW device 10 (i.e., the conventional SAW device as illustrated in FIG. 1 with its several detailed components not shown in FIG. 2) mounted on a compliant member (also referred to herein as an interface member) 40 that is in turn mounted on a material-under-test or body-under-test 42. The body-under-test 42 is subject to compressive or tensile stress forces as indicated by arrowheads 46.

The strain of the body-under-test 42 is converted to an applied stress on the SAW device 10 via the interface member 40. By choice of materials and shapes of the interface member 40 (e.g., comprising an elastic material) the conversion of strain on the body-under-test to stress on the SAW device is controlled and limited to a strain value in the SAW device that is below the elastic limit of the substrate of the SAW device.

The interface member 40 is interposed to absorb the extension or compression of the body-under-test 42 without fracturing the SAW device. Further, the tension and compression characteristics of the interface member 40 are known and thus the amount of stress or strain experienced and measured by the SAW device 10 can be converted to the amount of stress or strain on the body-under-test 42.

The forces indicated by arrowheads 46 cause a strain or deformation in the body-under-test 42. That strain in turn imposes a deformation or strain in the interface member 40 that creates a stress force on the interface member. Finally, the strain in the interface member 40 imposes stress forces on the SAW device 10. Those stress forces create a strain or deformation in the substrate 24 (see FIG. 1). That substrate strain is indicated by characteristics (e.g., period or frequency) of the reflected acoustic wave 34 (see FIG. 1) propagating in the SAW device 10.

Stress and strain are related by a modulus of elasticity (Young's Modulus) for a specific material.

$$\sigma = \epsilon E$$

where $\sigma$ is the stress force imposed on a material, $\epsilon$ is the resulting strain deformation and E is the modulus of elasticity of the material.

As is known, if forces are exerted on two connected bodies the strain of each is determined by a ratio of the elastic moduli of each material.

As related to the present invention, stress forces imposed on a lower surface of the interface member 40, and the resulting strain, is transferred to the SAW sensor 10 through the bulk of the interface member. Deformation of the upper surface of the interface member is constrained by a lower surface of the SAW sensor, which has a higher modulus than the interface member.

This arrangement can be modeled by finite elements methods or modeled in closed form. The latter technique is referred to as "virtual work" where one determines the strain in each member and translates that strain into work by force (a product of displacement and modulus) multiplied by distance (displacement). The work done is then in direct proportion to the strength of the bodies.

The governing boundary conditions in the configuration of FIG. 2 are that the lower surface of the interface member 40 must have the same strain (deformation) as the upper surface of the body-under-test 42 and the upper surface of the interface member 42 must have the same strain as the lower surface of the SAW sensor 10.

One can also assume, in a less elegant approach, that the distortion of the SAW sensor 10 is linear and well-behaved and that the interface member 40 also has a linear stress-strain function throughout its entire range of deformation. One can then find the force applied to the upper surface of the interface member and then determine the strain of the SAW sensor 10 as a function of the strain of the interface member and the body-under-test 42. Of course these simplifying assumptions are not perfectly linear, but the linear calculations based solely on geometry and the moduli of the materials comprising the SAW sensor and the interface member produce acceptable results in most applications.

Note that according to this technique it is not necessary to know the modulus of the underlying body-under-test 42 as the work exerted on the SAW sensor 10 by the body-under-test is minimal and can be ignored in most cases, especially if the modulus of the body-under-test 42 is about equal to or higher than the modulus of the SAW sensor 10. Thus the SAW sensor does not impact the strain of the material-under-test to any great extent.

Generally, the body-under-test 42 is influenced by the combined effect of the interface member 40 and the SAW sensor 10. The body-under-test is only "aware" of the forces/strains imposed at the interface with the interface member 40 and thus these forces/strains are effectively a combination of the moduli of the interface member 40 and the SAW sensor 10. Also, these forces/strains must consider the area of the interface. But generally, these forces/strains can be ignored as they have a very small effect on the strain of the body-under-test 42. But one should also consider how the added "strength" of the combined SAW sensor and interface member affects the local strain of the body-under-test.

But if the modulus of the body-under-test 42 is lower than the modulus of the interface member 40 then the characteristics of the interface member modify the strain of the body-under-test in an interface region of the interface member and the body-under-test. In this case the SAW sensor and interface member effectively add "strength" to the body under test at the interface or attachment region.

In a case where a material of the interface member 40 is softer or more pliable (lower modulus) than the body-under-test 42, the influence of the attached interface member and SAW sensor on the strain of the body-under-test is not significant and in many cases can be ignored.

For example, if the SAW sensor 10 is attached directly to a rubber band the relatively stiff and strong sensor does not permit the rubber band to deform in a region where the two are attached. In this configuration the measurements determined by the SAW sensor are difficult to correlate to deformation of the rubber band.

But if a rubber band is attached to a steel body and the steel body is stretched, the rubber band has little (or no) effect on deformation of the steel.

Returning to the features of the present invention, the interface member 40 is analogous to the rubber band in the example immediately above and does not adversely affect the strain of the body-under-test 42, but the interface member translates sufficient stress, as imposed on the body-under-test, to the SAW sensor 10 for measuring.

Figure 3:
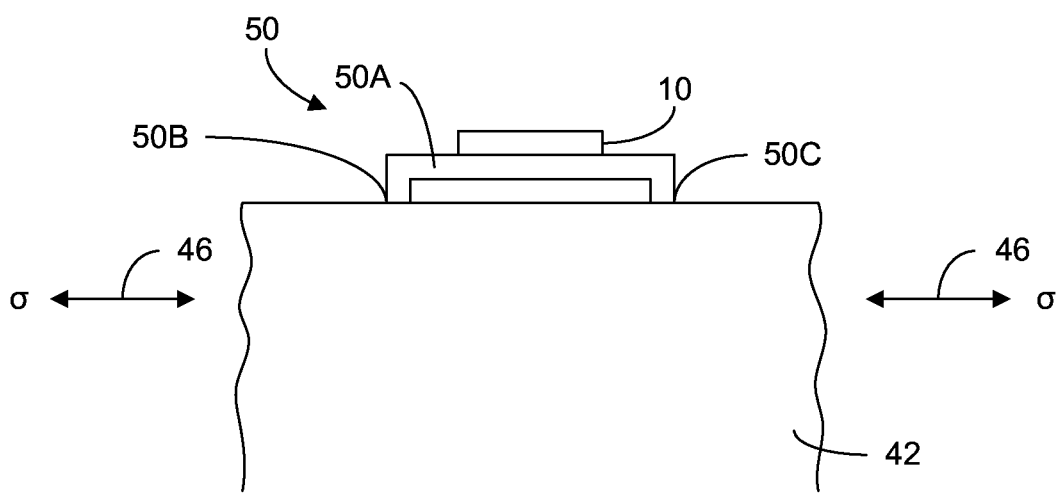

FIG. 3 illustrates another arrangement of components for determining the strain experienced by the body-under-test 42. According to this embodiment an interface member 50 comprises a connecting member 50A and two spaced-apart legs 50B and 50C. The legs are attached to the body-under-test 42.

As in the other embodiments described herein, the strain of the body-under-test is transferred through the interface member 50 for measuring by the SAW device 10.

According to another embodiment (see FIG. 4) an interface member(s) between the body-under-test and the SAW device converts the strain deformation (from which the stress forces can be determined) from a tensile force in the body-under-test to a compressive force in the SAW device, or vice versa. Either a conversion from tensile to compressive or from compressive to tensile is selected to obtain the most accurate measurements of the forces imposed on the body-under-test.

Figure 4:
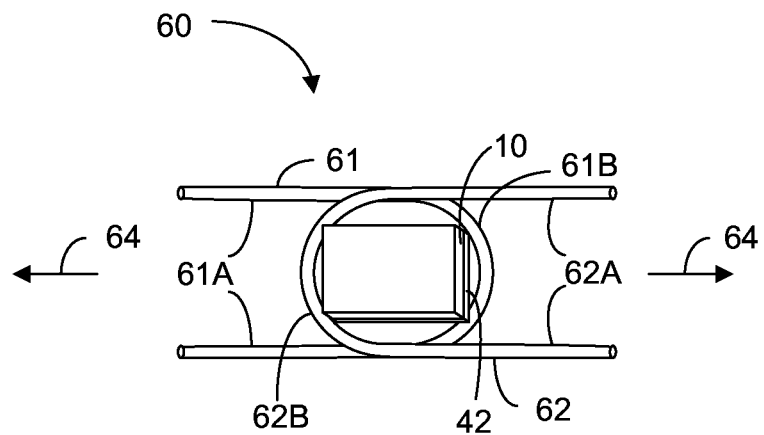
FIG. 4 illustrates components for transforming a compressive force to a tensile force.

FIG. 4 illustrates an apparatus 60 for converting tension of the body-under-test 42 to compression in the SAW device 10, where the body-under-test 42 is attached to a lower surface of the SAW device 10.

Two U-shaped components 61 and 62 each comprise two spaced-apart arm segments 61A/62A joined by a connecting segment 61B/62B. The components 61 and 62 encircle, in an opposing intersecting configuration, the body-under-test 42 as shown in FIG. 4.

Arrowheads 64 indicate the application of tensile forces to the components 62. According to the configuration of the components 62 relative to the body-under-test 42, the tensile forces on the arms are converted to compressive forces on the body-under-test 42.

These compressive forces create strain or deformation of the body-under-test 42 and that strain imposes stress forces on the SAW device 10. The stress forces create deformation in the SAW device 10 (specifically in the substrate of the SAW device) and these deformations are sensed by the SAW device as a change in the amplitude, frequency or period of the reflected SAW signal, as discussed above. See also FIG. 1.

Figure 5:
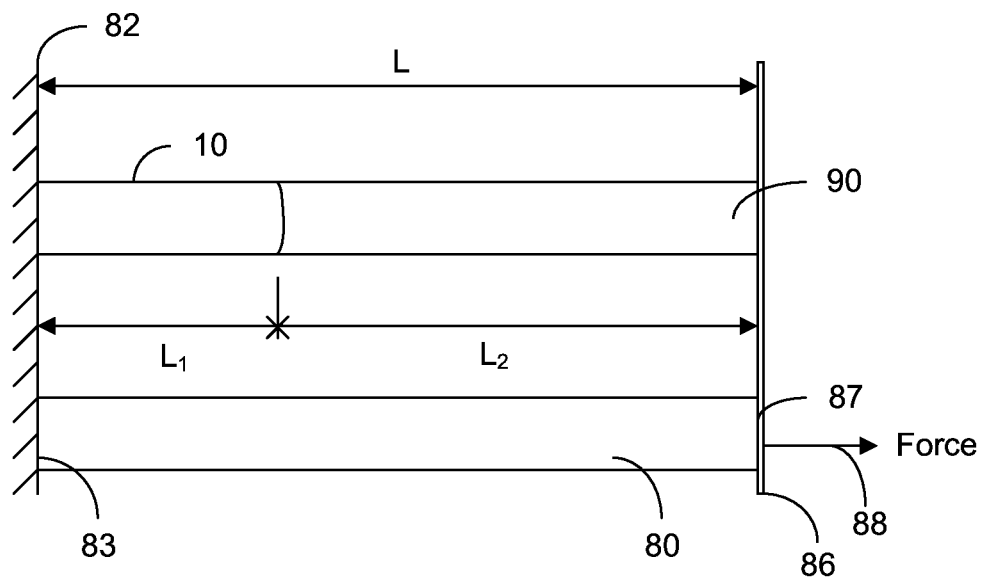
FIGS. 5 and 6 illustrate serially-configured components for measuring strain of a body-under-test.

FIG. 5 illustrates yet another embodiment comprising a body-under-test 80 disposed between and attached to a fixed surface 82 at an anchor point 83 and to a moveable member 86 at an anchor point 87. A force represented by an arrowhead 88 is applied to the moveable member 86 and transferred to the body-under-test 80.

An interface member 90 and the SAW sensor 10 are serially connected and also suspended between the fixed surface 82 and the moveable member 86.

As the body-under-test 80 experiences a tensile force, as indicated by the arrowhead 88, that force is also exerted on the interface member 90 and transmitted to the SAW device 10. As a result, the body-under-test 80, the interface member 90 and the SAW sensor 10 each undergo a strain deformation.

In the example analyzed herein, it is assumed that the interface member 90 has the same cross sectional area but a different elastic modulus from the SAW sensor 10. As can be seen, a combined strain experienced by the interface member and the SAW sensor is the same as the strain experienced by the body-under-test.

The body-under-test 80 is subjected to a force as represented by the arrowhead 88 and the strain experienced by the SAW sensor is determined based on, for example, a period of the SAW reflected wave. The strain in the body-under-test is determined as follows.

In the equations below, $\epsilon$ represents the strain of a body, L represents a length measure, E represents a modulus and $\sigma$ represents a stress force. In each case a subscript "s" refers to the SAW sensor and a subscript "c" refers to the compliant or interface member.

The force changes the length by $\Delta L$, resulting in a strain of $\Delta L/L = \epsilon$ The strain value $\epsilon$ is determined by the SAW sensor 10. It is assumed that the measured signal is proportional to the strain of the entire SAW device since the SAW device is comprised of uniform material and has a uniform cross section.

The strain of the body-under-test 80 is a sum of SAW device strain and the interface member or compliant member strain. Expressed as:

$$\epsilon = \epsilon_s + \epsilon_c$$

Also, $L = L_s + L_c$ and $\Delta L = \Delta L_s + \Delta L_c$

If $\epsilon_s$ and $\epsilon_c$ can be determined, then $\epsilon$, the strain in the body under test, can be found.

Since the cross section of the interface or compliant member and the SAW sensor are the same, the stress in the SAW sensor and the stress in the interface or compliant member are the same, because the force is applied through the series combination of the SAW sensor and the interface or compliant member and the force is a through variable.

We know $$\sigma = E \epsilon \text{ thus}$$

$$\sigma_s = E_s \epsilon_s \text{ and } \sigma_c = E_c \epsilon_c$$

Since the sensor and compliant member are serially connected and have the same cross sectional area, $$\sigma_s = \sigma_c, \text{ and so}$$

$$E_s \epsilon_s = E_c \epsilon_c \text{ and rearranging}$$

$$\epsilon_c = E_s \epsilon_s / E_c \text{ and substituting again}$$

$$\epsilon = \epsilon_s + E_s \epsilon_s / E_c \text{ or}$$

$$\epsilon = \epsilon_s (1 + E_s/E_c)$$

Since both the moduli of the sensor and compliant member $E_s$ and $E_c$ are known, and the sensor strain $\epsilon_s$ is measured, the strain on the body-under-test $\epsilon$ can be found from the equation immediately above.

Note that the SAW sensor measures only a portion of the sensor strain (i.e., between the interdigital transducer 20 and the reflector array 30 of FIG. 1. From this measured value the strain of the entire sensor ($\epsilon_s$) can be determined.

Figure 6:
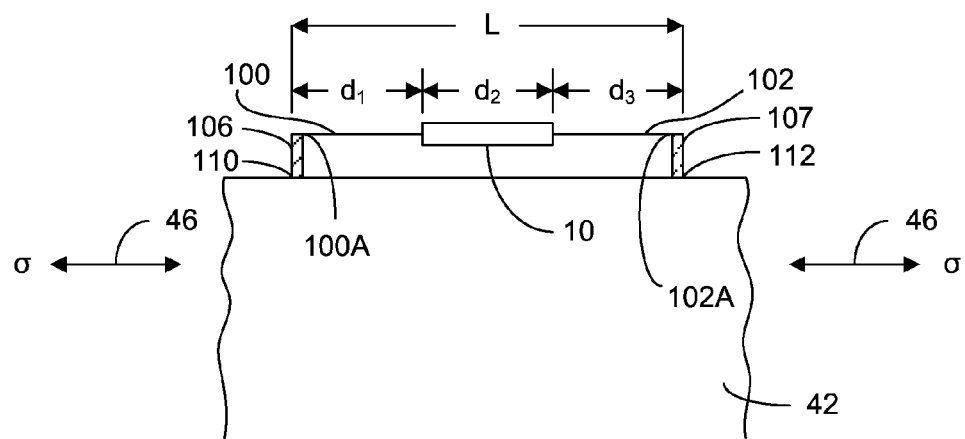

FIG. 6 illustrates yet another embodiment for measuring strain on the body-under-test 42.

Compliant members (or interface members) 100 and 102 and the SAW sensor 10 have respective lengths of d1, d3 and d2 as shown. An arm 106 at an end 100A of the compliant member 100 is attached to the body-under-test 42 at an anchor point 110. An arm 107 at an end 102A of the compliant member 102 is attached to the body-under-test 42 at an anchor point 112.

Calculations for determining the strain in the body-under-test 42 are set forth below.

$\Delta L/L$ is the strain in the body under test $\Delta d_2/d_2$ is the strain experienced by the SAW device $\Delta d_1/d_1$ and $\Delta d_3/d_3$ are strains in the compliant members 100 and 102 respectively $$\Delta L = \Delta d_1 + \Delta d_2 + \Delta d_3$$

If we limit the quantity $\Delta d_2/d_2 = 0.001$ maximum (a realistic value for SAW device strain), we can then solve for $\Delta d_1/d_1$ and $\Delta d_3/d_3$ by materials properties and geometry.

$\Delta d_2/d_2 = 0.001$ maximum implies $\Delta d_2$ single $d_2$ is "designed."

Assuming a simple case of symmetry, $\Delta d_1 = \Delta d_3$ and $d_1 = d_3$ or $\Delta d = \Delta d_2$ (known)$+2 \Delta d_1$ This allows a choice of a material (providing Young's modulus) and the design of a shape ($\sigma = E \epsilon$) for the arms 106 and 107.

Figure 7:
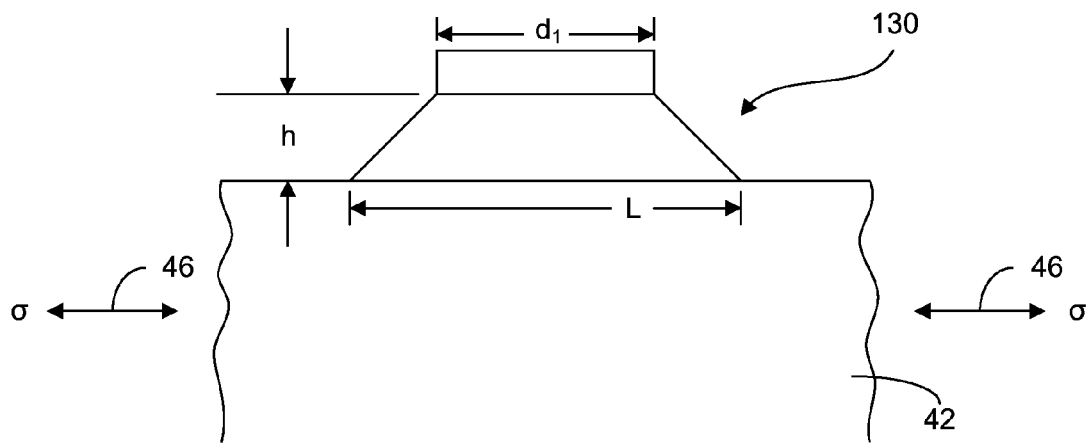
FIG. 7 illustrates components for measuring stress of the resulting strain on a body-under-test.

While the embodiment of FIG. 7 poses a more difficult case for a large strain, the concept is similar.

Strain in sample=ΔL/L

Strain in sensor=$\Delta d_1/d_2$ <0.001

For FIG. 7 one selects a design variable "h" based on materials properties of a compliant member 130 and the desired sample measurement range.

The embodiments illustrated in FIGS. 2 and 7 are similar, i.e., deformation of the body-under-test is transferred to strain (stress) in the SAW device through a material having a relatively lower modulus, hence reducing the effective strain that is applied to the SAW sensor.

Another technique for confining the strain to a specific range is to change the cross sectional area, such as is done for common stress strain testing. Since the force is constant across the length, and since strain and stress are both functions of force per unit area, any change in this area influences the strain or stress.

This technique can be used to enhance the strain in the strain sensor when it is desired to measure very small strains, or to reduce the strain to avoid breaking the crystal.

In one embodiment, nickel titanium alloys, such as nitinol, which exhibits a very unusual stress strain behavior, can be used to enhance small strain and still avoid failure of the SAW device crystal. Nitinol has a linear stress-strain behavior for small stresses, but a very non-linear stress-strain behavior for high stresses. If the cross sectional area of the nitinol is properly designed, it will enhance the strain sensitivity for small strains while reducing the stress in the lithium niobate crystal for larger strains.

The various embodiments of the present invention use a piezoelectric crystal, which has very low strain-to-failure relationship, to measure the strain of materials that have much larger strain-to-failure characteristics. The strain of the material under test must be reduced in a proportional and a calculatable manner such that the SAW device can withstand the stress that it experiences. Thus a material "buffer" (e.g., an interface member or a compliant member) is interposed between the test subject and the SAW device.

Those skilled in the art know that strain deformation can also result from temperature changes. In one embodiment, an initial strain measure can be used to null out the effects of temperature on the body-under-test.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

I claim:

1. A strain sensor for determining a strain experienced by a body under test, in response to forces exerted on the body-under-test, the strain sensor comprising:
   an interface member mounted on a surface of the body-under-test;
   a SAW sensor comprising a substrate mounted on a surface of the interface member, wherein the strain in the body-under-test is translated to strain in the substrate via the interface member, and the strain in the body-under-test is determined from the strain of the substrate; and
   wherein the strain imposed on the substrate is below an elastic limit of the substrate and the strain imposed on the interface member is below an elastic limit of the interface member, and wherein a first surface of the interface member in contact with a first surface of the body-under-test experiences the same strain as the first surface of the body-under-test, and wherein a first surface of the substrate in contact with a second surface of the interface member experiences the same strain as the second surface of the interface member.

2. The strain sensor of claim 1 wherein the stress forces comprise one of tensile forces or compressive forces.

3. The strain sensor of claim 1 wherein a material and a shape of the interface member determines stress forces imposed on the substrate responsive to strain of the body-under-test.

4. The strain sensor of claim 1 wherein the interface member comprises an inverted U-shaped member further comprising first and second spaced-apart legs connected by a connecting member, the first and second legs connected to the member under test.

5. The strain sensor of claim 1 wherein the strain in the SAW sensor is less than the strain in the body-under-test.

6. The strain sensor of claim 1 wherein the strain of the body-under-test is translated to a strain in the SAW sensor through the interface member, the SAW sensor determining the strain in the SAW sensor from which the strain in the body-under-test can be determined.

7. The strain sensor of claim 6 wherein forces exerted on the body-under-test can be determined from the strain in the body- under-test.

8. The strain sensor of claim 1 wherein the first surface of the body-under-test and the second surface of the interface member are parallel.

9. The strain sensor of claim 1 wherein the interface member modifies the strain imposed on the SAW device by forces exerted on the body-under-test.

10. The strain sensor of claim 1 wherein the body-under-test, the interface member and the SAW sensor are disposed in a stacked configuration, with the interface member between the body-under-test and the SAW sensor.

11. The strain sensor of claim 1 wherein the strain in the SAW sensor is determined responsive to one or more of an amplitude, frequency and period of a reflected wave within the SAW sensor.

12. The strain sensor of claim 1 wherein the interface member reduces the strain induced in the SAW sensor from the body-under-test under compression or tension forces, or the interface member increases the strain induced in the SAW sensor from the body-under-test under compression or tension forces.

13. A strain sensor for determining a strain imposed on a body-under-test in response to forces exerted on the body-under-test, the strain sensor comprising:
   a first interface member, a SAW sensor comprising a substrate, and a second interface member forming a serial string with the SAW sensor between the first and second interface members;
   the serial string connected between first and second locations on a body-under-test;
   wherein strain in the body-under-test is translated to strain in the substrate through the first and second interface devices and determined by the SAW sensor, wherein from determined strain in the SAW sensor the strain in the body-under-test can be determined; and
   wherein the strain imposed on the substrate is less than an elastic limit of the substrate.

14. The strain sensor of claim 13 wherein a cross section of the first and second interface members and a cross section of the SAW sensor are equal.

15. The strain sensor of claim 13 wherein the first and second interface members reduce the strain induced in the substrate from the body-under-test under compression or tension forces, or the first and second interface members increase the strain induced in the substrate from the body-under-test under compression or tension forces.

16. A strain sensor for determining a strain experienced by a body under test in response to forces imposed on the body-under-test, the strain sensor comprising:
   a first end of the body-under-test attached to a fixed surface and a second end of the body-under-test attached to a moveable surface;
   an interface member and a SAW sensor serially configured and attached between the fixed surface and the moveable surface; and
   wherein from a strain measured by the SAW sensor, a strain experienced by the body-under-test can be determined.

17. The strain sensor of claim 16 wherein a cross section of the interface member and a cross section of the SAW sensor are equal.

18. The strain sensor of claim 16 wherein the strain measured by the SAW sensor is determined responsive to one or more of an amplitude, frequency and period of a reflected wave within the SAW sensor.

19. The strain sensor of claim 16 wherein the interface member reduces the strain induced in the SAW sensor from the body-under-test under compression or tension forces, or the interface member increases the strain induced in the SAW sensor from the body-under-test under compression or tension forces.

* * * * *